US006421588B1

(12) United States Patent
Janata

(10) Patent No.: US 6,421,588 B1
(45) Date of Patent: Jul. 16, 2002

(54) SELF-DIAGNOSTIC SYSTEM FOR CONDITIONED MAINTENANCE OF MACHINES OPERATING UNDER INTERMITTENT LOAD

(75) Inventor: Jiri Janata, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/638,294

(22) Filed: Aug. 14, 2000

Related U.S. Application Data

(63) Continuation-in-part of application No. 09/192,707, filed on Nov. 16, 1998, now Pat. No. 6,128,561.

(51) Int. Cl.[7] .......................... G01D 21/00; F01M 11/12
(52) U.S. Cl. ........................ 701/29; 701/30; 340/438; 340/439; 340/450.3; 340/457.4; 73/117.3
(58) Field of Search ............................. 701/29, 30, 35; 340/438, 439, 449, 450.3, 457.4; 73/53.05, 117.3; 324/663, 667

(56) References Cited

U.S. PATENT DOCUMENTS

| 4,506,337 A | * | 3/1985 | Yasuhara | 701/30 |
| 4,706,193 A | * | 11/1987 | Imajo et al. | 701/30 |
| 4,862,393 A | * | 8/1989 | Reid et al. | 701/30 |
| 4,970,492 A | * | 11/1990 | King | 701/30 |
| 5,382,942 A | * | 1/1995 | Raffa et al. | 701/30 |
| 5,633,796 A | * | 5/1997 | Cullen et al. | 701/30 |
| 5,750,887 A | * | 5/1998 | Schricker | 73/117.3 |
| 5,824,889 A | * | 10/1998 | Park et al. | 701/29 |
| 5,969,601 A | * | 10/1999 | Sato et al. | 701/30 |
| 6,128,561 A | * | 10/2000 | Janata | 701/29 |
| 6,253,601 B1 | * | 7/2001 | Wang et al. | 73/117.3 |

* cited by examiner

*Primary Examiner*—Gary Chin
(74) *Attorney, Agent, or Firm*—Thorpe North & Western, LLP

(57) ABSTRACT

A system and method for determining the condition of lubricating oil in an oil-utilizing mechanism, said system comprising: sensor means for sensing the chemical composition of oil vapor in the head space of the oil reservoir, or a holding reservoir; temperature probes for sensing the temperature of the oil and of the sensor means; microprocessor means connected to the sensor means and temperature probes for creating a vapor signature by means of a pattern recognition algorithm representing the chemical composition of the vapor in the head space; and display means for producing a discernable indication to an operator if the processor means determines that the vapor signature deviates from predetermined baseline parameters. The system is initiated when the oil-utilizing mechanism is shut off, or when a sample of oil is taken from the oil reservoir and placed in the holding reservoir, and senses conditions periodically during cool-down of the oil.

23 Claims, 5 Drawing Sheets

SELF-DIAGNOSTIC SYSTEM FOR CONDITIONED MAINTENANCE OF MACHINES OPERATING UNDER INTERMITTENT LOAD

The present application is a continuation-in-part of co-pending U.S. patent application Ser. No. 09/192,707, filed on Nov. 16, 1998, now U.S. Pat. No. 6,128,561.

BACKGROUND OF THE INVENTION

1. Field of the Invention

The present invention relates to a self-diagnostic system for determining maintenance conditions of lubricants in oil-utilizing machines operating under intermittent loads. More particularly, the present invention relates to a system and method for determining the condition of oil in an engine, transmission, or the like, in order to optimize oil maintenance intervals.

2. State of the Art

Lubricating oils are typically comprised of high molecular-weight products of the petroleum distillation process. The base constituents of these oils are typically hydrocarbon chains having anywhere from 16 to 30 carbon atoms, and a boiling point higher than 350° C. Undesired constituents such as tars, asphalts, greases, and paraffin waxes are preferably removed during the refining process, and certain additives such as thickening agents, detergents, and anti-oxidants may be added to impart desired properties to the oil.

As oil is used in the high temperature, high stress environment of an internal combustion engine or other oil-utilizing machine, the base hydrocarbons tend to break down over time. Typically, the relatively long hydrocarbon chains of the base oil break up and degrade into oxidized forms of hydrocarbons such as polyacohols, aldehydes, carboxylic acids, esters, etc., which have inadequate or undesirable properties. When some significant proportion of the base oil has broken down in this way, the oil will no longer protect the machine from damage as desired.

At present, oil changes in internal combustion engines and similar oil-utilizing machines are typically performed according to the mileage or hours of operation of the machine, not according to the directly identified needs given by the chemical state of the lubricating oil. However, it will be appreciated that the miles driven or hours of use do not necessarily indicate the condition of the oil. For example, operation under heavy or rapidly varying loads, or under dusty or extreme temperature conditions will tend to cause oil to break down sooner than otherwise. A mileage or time-based schedule is thus only an approximation of the actual needs, based on numerous assumptions. The result is that the lubricating oil may be changed too infrequently, resulting in accumulated damage to the mechanical parts, or it may be changed more often than needed, causing needless maintenance expense and producing excessive waste oil. While one could periodically remove a sample of oil from a vehicle's oil reservoir and have it chemically tested, this is so time consuming, expensive, and inconvenient as to be essentially impractical.

It would be desirable to have a self-diagnostic system that could sense the actual chemical condition of the lubricating oil in intermittently operated machines, and provide an operator or maintenance person with an indication when the oil has reached a certain point of chemical degradation.

OBJECTS AND SUMMARY OF THE INVENTION

It is therefore an object of the present invention to provide a system for detecting the chemical condition of lubricating oil within the oil reservoir of an intermittently operating machine, such as an internal combustion engine, in order to determine the maintenance needs of the lubricant.

It is another object of the invention to provide an informational display indication that will notify a user when the lubricating oil is degraded beyond a specified point, to thus allow prompt replacement of the oil.

It is another object of the invention to provide a system for detecting the condition of lubricating oil within the oil reservoir of an internal combustion engine by a sampling/analysis sequence which is initiated when the engine is switched off and which sequence continues during engine cool-down.

It is yet another object of the invention to provide a system for sensing the composition of vapors in the head space of an oil reservoir where most sensor data acquisition occurs during the period when the engine is not in operation.

The above and other objects are realized in a system and method for determining the condition of oil in an oil-utilization mechanism which has an oil reservoir having a head space above the oil, said system comprising: a sensor means for sensing the composition of vapor in the head space and for developing a signal representing said composition; a processor for receiving the signal and for determining if the signal corresponds to predetermined parameters; and apparatus for producing a discernable indication if the processor determines that the signal deviates from the predetermined parameters.

In accordance with one aspect of the invention, a system for sensing the composition of vapors within an oil reservoir of an internal combustion engine initiates a sampling/analysis sequence when the engine is switched off, which sequence continues during engine cool-down.

In accordance with another aspect of the invention, a sample of oil is removed from the oil reservoir of a continuously running machine and deposited in a holding reservoir. A sampling/analysis sequence of the vapors within a head space of the holding reservoir is initiated when the oil sample is placed in the holding reservoir, and continues as the oil sample cools down.

Other objects and features of the present invention will be apparent to those skilled in the art, based on the following description, taken in combination with the accompanying drawings.

DETAILED DESCRIPTION OF THE PREFERRED EMBODIMENT

Figure 1:
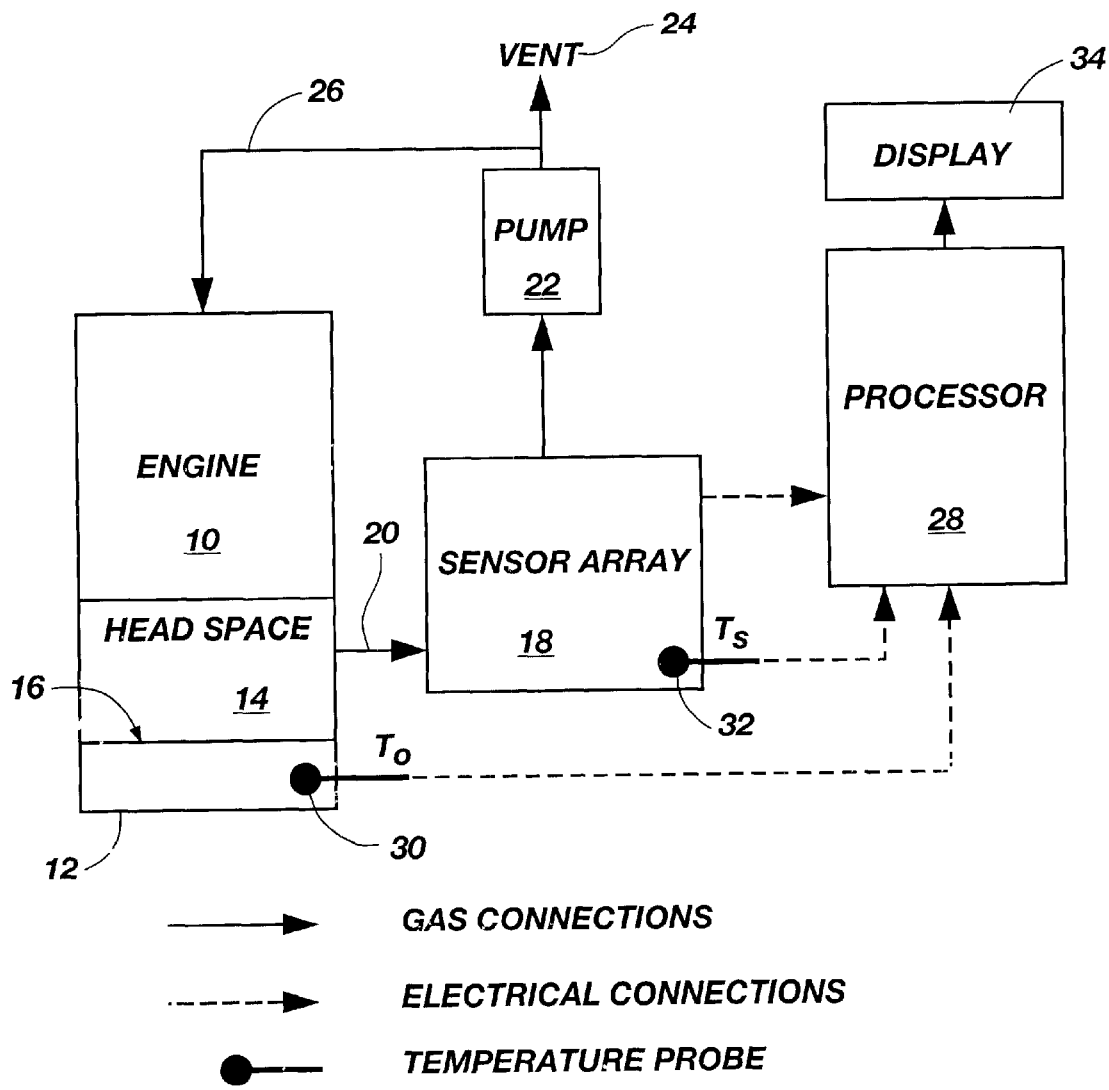
FIG. 1 is a schematic diagram of one embodiment of the self-diagnostic system of the present invention installed in an internal combustion engine.

FIG. 1 is a schematic diagram of one embodiment of the self-diagnostic system of the present invention. Shown is an engine 10 with an oil reservoir 12, such as the crankcase of the engine, having a head-space 14 above the free surface 16 of the oil. Alternatively, it will be apparent that instead of an engine, the present invention could be used in a transmission of an internal combustion engine, a gas turbine engine or jet engine, a hydraulic machine, or any other oil-utilizing machine subject to intermittent use and having an oil reservoir.

A sensor array 18 is disposed in communication with the head space 14 via a conduit 20 which will allow the head-space vapors to travel to the array for sampling. The vapors are transported through the conduit 20 by means of a micropump 22 which creates suction to draw the vapors to and through the sensor array. The vapors are then exhausted to the outside through a vent 24 after sensing. Alternatively, if required for environmental or other reasons, the vapors may be circulated back into the engine, for example for combustion, through another conduit 26.

The mixture of volatile degradation products in the head-space above the lubricant represents a chemical signature that identifies the composition, i.e., the state of the oil. As noted above, these degradation products of the oil are typically oxidized forms of hydrocarbons including C6–C20 aliphatic carboxylic acids, C6–C14 carboxylic aldehydes, C6–C14 aliphatic esters, and C6–C12 unsaturated aldehydes. The degradation products may also include aromatic acids, aromatic aldehydes, and polycondensed aromatic hydrocarbons. Antioxidants may also be present, which gradually disappear as the oil degrades. Chemical changes taking place in the lubricating oil may be detected by sensing the changes of composition of these volatile degradation products in the gas phase (head-space) above the lubricant. As will be apparent to one knowledgeable in the field, the presence of these degradation products increases as the oil becomes progressively more degraded over time. These volatile combustion products are in a dynamic equilibrium with the components of the oil and indicate the status of the lubricant, i.e. the need for replacement.

The sensing array 18 preferably consists of 6 to 10 sensing elements, each preferably sensitive to a different degradation component of the oil. A greater number of sensing elements (i.e. more than 10) could be provided if desired for more complete and accurate sampling of the head-space vapors, but are not necessary for adequate implementation of the present invention. The sensing elements may be electrochemical, optical, mass, thermal, or any combination thereof to form an array. The preferred sensor type is an electrochemical sensor which detects conductivity changes. See J. Janata, *Principles of Chemical Sensors* (New York, Plenum Press, 1989). One example of such a sensor is a semiconducting tin oxide type sensor such as the Figaro TGS series available from Figaro Engineering, Inc., Japan.

The detected change of the head-space composition constitutes a typical chemical signature corresponding to the state of the lubricant. Fresh oil also has a characteristic signature which, in the conditioned-maintenance system of the present invention, represents the baseline against which the progressive degradation is measured.

The sensor array 18 is connected to a microprocessor 28 which receives signals from the various sensing elements. The processor 28 also receives signals from a temperature probe 30 disposed in the oil reservoir 12 to detect the temperature of the oil, and from another temperature probe 32 disposed adjacent to the sensor array 18 to detect the temperature of the sensor array. The oil reservoir temperature probe 30 is important to the system of the present invention because the rate of change of the composition head-space vapors varies as a function of the temperature of the oil. The sensor array temperature probe 32 is employed because the performance of the sensor array depends in part on its operating temperature, which may vary significantly from the temperature of the oil.

Figure 2:
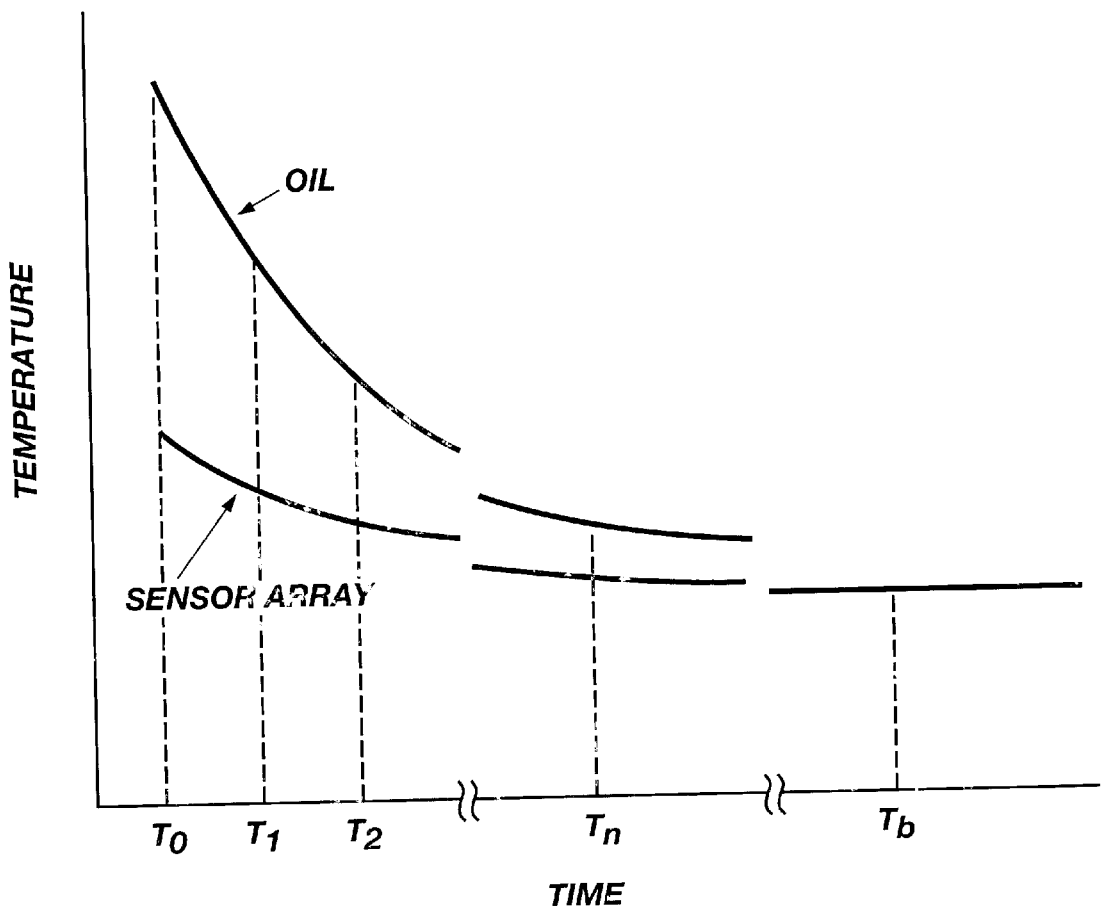
FIG. 2 is a graph of an illustrative cool-down temperature curve of engine oil and sensor array of an internal combustion engine beginning at engine shut-down.

The sensing array will absorb heat from the engine and from the head-space vapors, but may be physically separated some distance from the engine itself, and typically will not attain the same temperature as the engine oil, as shown by the curve of FIG. 2. Consequently, the cooling curve response profile must be corrected for the effects of the temperature changes of the sensing array itself, which should be independently measured. Those skilled in the art will recognize that correcting the response profile can be easily done by normalizing the cooling curve to the difference in temperature between the oil and the sensing array.

Additionally, the performance of most sensors is degraded when they must operate under vibration. This is particularly true of mass sensors. Because the invention here described acquires data when the engine is not in operation, it operates in an essentially vibration free environment. It will be apparent that this configuration will enhance both the performance and useful life of the sensors. Moreover, by operating when the engine is not in use, a generous amount of time is made available for data acquisition and data processing.

The microprocessor 28 analyzes the signals transmitted to it, and provides output in a user-friendly format such as through an indicator light, CRT, or other visual display 34, or alternatively, through other indications such as audible signals, to notify the user or maintenance personnel of the condition of the oil. It will be apparent to those skilled in the art that other modes of output may also be advantageously employed to accomplish the same purpose.

The system of the present invention uses a novel sampling/analysis sequence, which may be initiated when the engine 10 is shut off or some preprogrammed delay time thereafter, and the oil begins to cool down. Alternatively, the invention can be used with continually running machines, as described in more detail below. A graph of the cool-down temperature curve of the engine oil and sensor array beginning at engine shut-down is provided in FIG. 2. As the temperature of the oil decreases after engine shut-down, the chemical composition of the head-space vapors changes according to the type and concentration of its volatile components. The most volatile components, such as aliphatic esters and alcohols, stay in the gas phase the longest, while the least volatile components, such as aliphatic acids and aldehydes, disappear. As noted above, the rate of these composition changes is a function of the temperature of the oil.

The response from the integrated chemical sensing array 18 is obtained at pre-determined temperature intervals during the cool-down phase, shown as $T_0$, $T_1$, $T_2$, and so forth in FIG. 2, and is evaluated by the on-board microprocessor 28 to determine a signature of the oil vapors. A three-dimensional representation of the time- and temperature-dependent dynamic vapor signature of the oil reservoir vapors is given in FIG. 3. In this figure the several discrete peaks represent the time and temperature dependent signature of the various constituent degradation products present in the oil vapor. The three-dimensional graph thus represents a landscape or signature of either "good" or "bad" oil. The absolute values, positions, or number of peaks in this landscape do not have any particular meaning except as an indication of the state of the oil. The mode of analysis is similar to the decision made by an experienced wine taster who does not know the composition of the wine, but can nevertheless determine the type, quality, and even the vintage of the product. This approach is commonly known as artificial intelligence or in the case of gas sensing, "electronic nose." The strategy for recognizing the patterns of like complex mixtures is called pattern recognition.

Figure 4:
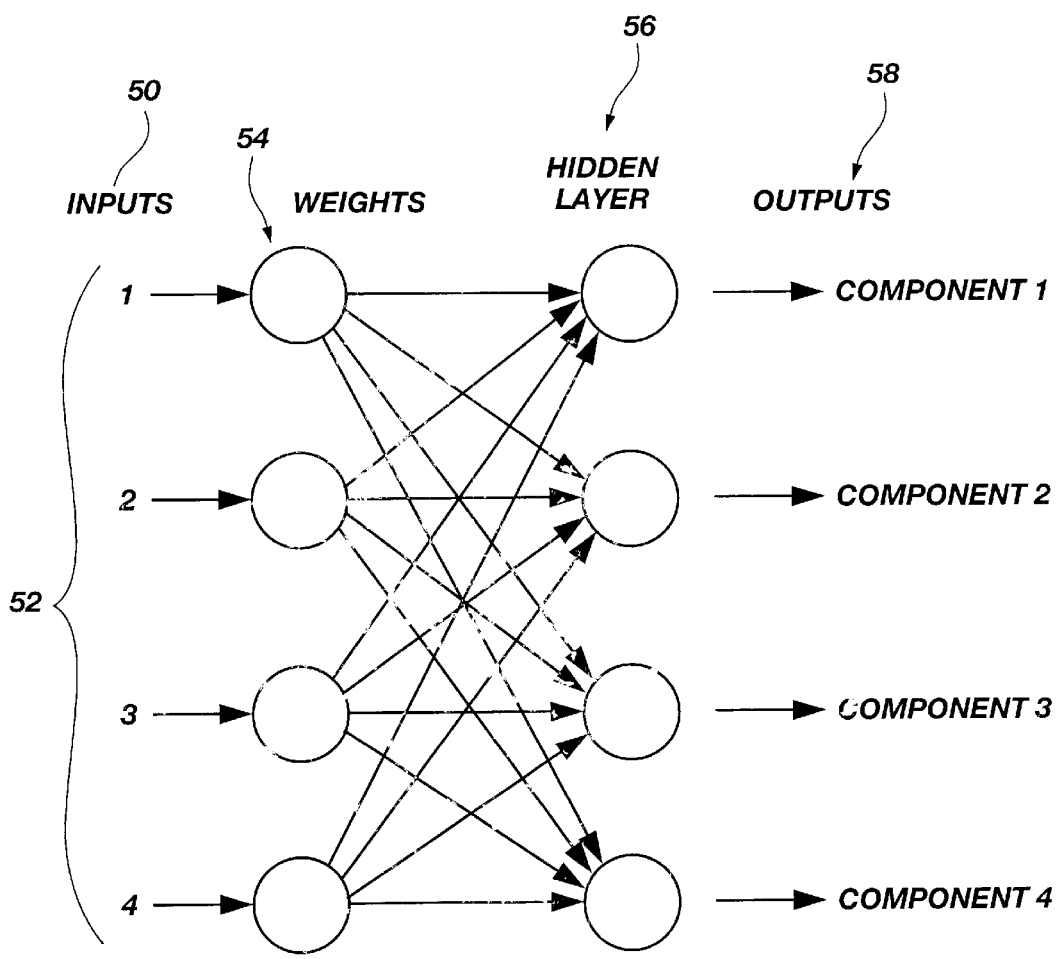
FIG. 4 is a schematic diagram of an artificial neural network for accepting inputs from a plurality of sensors in order to create a dynamic vapor signature.

There are several pattern recognition packages available to perform this task. One such technique is called Artificial Neural Networks or ANN. See D. E. Rumelhart, G. E. Hinton, R. J. Williams, "Learning Representations by Back Propagating Erros", 323 Nature 533–536 (1986). A scheme for ANN as part of the present invention is shown in FIG. 4. Raw inputs 50 from an array 52 consisting of a plurality of sensors (four sensors shown for simplicity) are fed into the first input layer of amplifiers 54. From there, the outputs are fed to a plurality of elements of hidden layer amplifiers 56 which multiply the inputs by a predetermined coefficient during the "learning" phase of the ANN. The "learning" is performed automatically by presenting the ANN with the mixture of known composition and adjusting the outputs from the output layer 56 to the desired values. The time- and temperature-dependent dynamic vapor signature of the oil vapors is determined by the configuration of the entire group of output values 58 at a plurality of sampling times during the sampling cycle.

This "learning" of the ANN is performed for the "good" oil and the values of the amplification factors are permanently stored, such as in computer memory, as the signature of the "good" oil. The ANNs can be implemented either in the software or in the hardware form. As noted, the absolute concentrations of individual degradation products in the head space or their algorithmic relationship to the composition of the oil is not necessary.

Another pattern recognition algorithm that may be advantageously employed in the present invention is called Visual Empirical Region of Influence (VERI), developed at Sandia National Laboratories. See G. C. Osbourn, J. W. Bartholomew, A. J. Ricco, and G. C. Frye, "Visual-Empirical Region-of-Influence Pattern Recognition Applied to Chemical Microsensor Array Selection and Chemical Analysis", 31 *Account of Chemical Research* 297–307 (1998). VERI computes distances between data points in the n-dimensional space (where n is the number of sensors in the sensing array).

The training or "learning" of this algorithm is similar to ANN, again based on the response of the array to the known standard. In both ANN and VERI pattern recognition techniques the deviation of the actual signature (i.e. progressively deteriorating oil) is compared with the baseline or standard signature (i.e. the "good" oil). The microprocessor "decision" whether to advise changing the oil or not is based on the chosen magnitude of acceptable deviation between "good" oil and "bad" oil.

Figure 3:
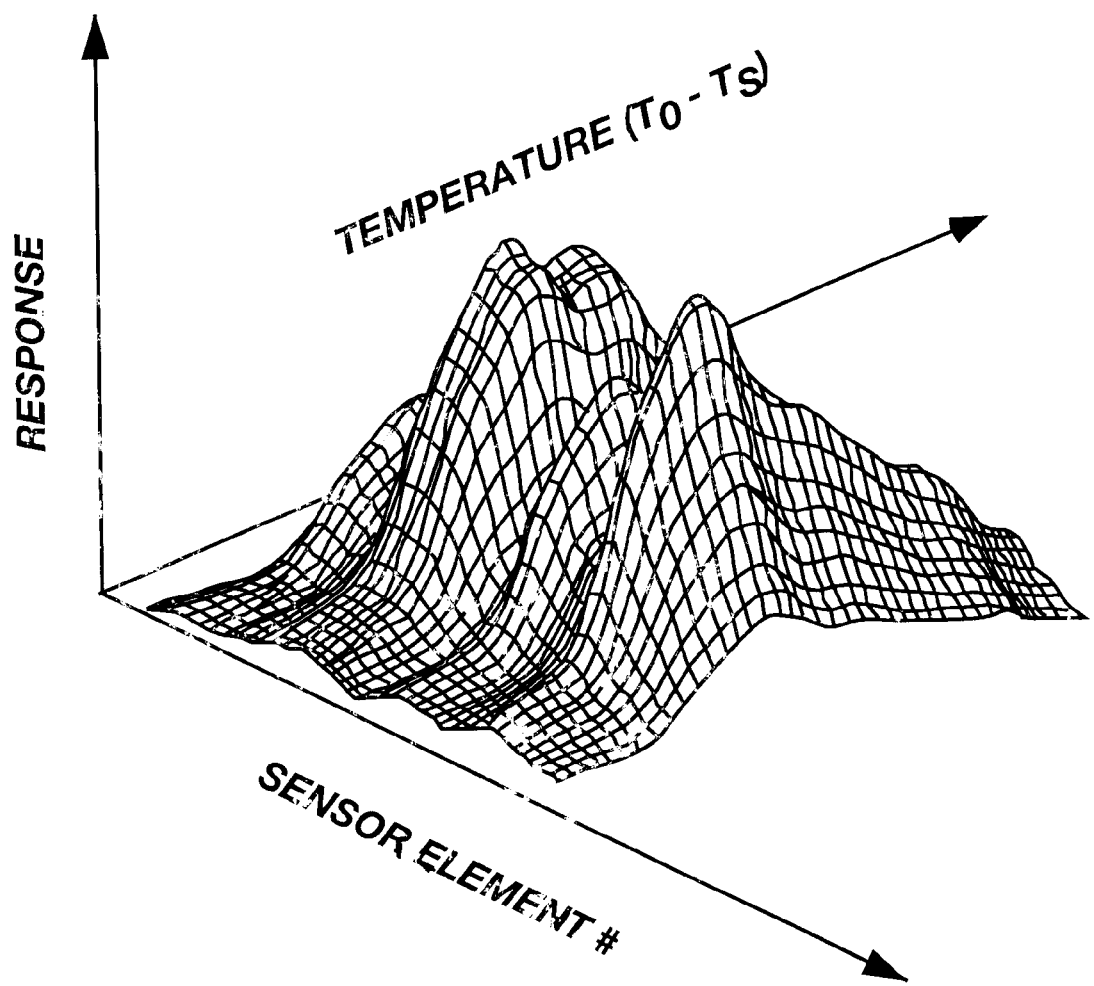
FIG. 3 is a representation of the three-dimensional time- and temperature-dependent dynamic vapor signature of the oil reservoir vapors.

The preferred diagnostic schedule would be as follows. The engine is operated for a minimum predetermined time and reaches a standard operating temperature. The corresponding temperature of the oil is $T_o$ (FIG. 2). The diagnostic sequence commences immediately after the engine ceases its operation (or when the oil sample is removed from the oil reservoir and placed in the holding reservoir). The response of the head-space changes is recorded at different points, $T_0$, $T_1$, $T_2$, etc., on the cooling curve (FIG. 2) This time-and-temperature-dependent "dynamic" information for each sensor becomes a part of the diagnostic test (FIG. 3).

After the oil cools down completely, the baseline value of the "signature" $T_b$ is obtained. Because of its design, the diagnostic system of the present invention is self-calibrating since the composition of the head-space under a cooled-down condition is expected to be constant or nearly constant. Both the "cold" and the "hot" signatures are compared to the "cold" and the "hot" signatures corresponding to the fresh oil, and the deviation of these signatures provides the desired information about the required lubricant change.

This information is made available in a user-friendly form prior to initiating the next duty cycle. The typical scenario for a motor vehicle, according to this scheme, can be described as follows: The vehicle is operated for a minimum required time and then parked. The diagnostic sequence starts immediately (or, alternatively, after a selected delay). The data is obtained and analyzed during the rest period, and after complete cool down the system calibrates itself. The microprocessor retains in memory the calibration signature, and the cycle is repeated again. The microprocessor compares the calibration signatures of the n'th and the n-1 run, and the results are made available to the operator prior to the next duty cycle with appropriate recommendations for action.

Monitoring of the chemical status of the oil is the great advantage of the present invention, and is the fundamental idea behind condition-based maintenance. Instead of following a necessarily approximate mileage or hours of operation schedule for oil changes, maintenance can be scheduled based on the directly identified needs given by the chemical state of the lubricant. Condition-based maintenance thus saves both labor and material costs in engine maintenance, as well as decreases the volume of pollutants such as waste oil discarded into the environment. The main distinguishing feature of the present invention is that the information acquisition is done dynamically by a multi-sensing array while the engine is not operating.

Another significant advantage of the present invention is the baseline time determination feature. The data collection of this invention relies on the time dependent changes of the head space composition (profile) collected after each duty cycle. Turning the engine off (or withdrawing the oil sample) provides a precise determination of t=0 from which the data acquisition during the cooling period begins. Thus, the time dependence of the profiles of the composition of the head space becomes the part of the signature of the "good" or "degraded" lubricant. The "zero time" aspect of this information acquisition prevents one notorious problem of chemical sensors/arrays: baseline drift. That is, each $T_n$=0 for the n-th profile establishes a new baseline. That type of information and such benefits would not be available for monitoring of the head space above the lubricants in continuously operating systems, e.g. in transformer oil because the profile at t=0 could not be accurately established.

The inventors have found that other classes of gaseous compounds are also present in the head space above used oil in addition to those mentioned above. For example, aromatic acids such as benzoic acid, aromatic aldehydes such as benzaldehyde, and polycondensed aromatic hydrocarbons such as napthalene and biphenyl may also be present in varying concentrations the gas phase above used oil. The inventors have configured sensors to detect these classes of compounds, and have included the concentration of these constituents in the time and temperature based vapor signature which signals the condition of the oil.

The inventors have also discovered that the disappearance of various antioxidants from the head space vapor is a further indication of degraded oil. Producers of lubricating oils routinely add antioxidants to slow the rate of oxidation of the hydrocarbons, thus slowing the rate of breakdown of these compounds. When these compounds are present in the oil, they will also have a representative vapor pressure which will cause them to be present in gaseous form in the head space of the oil reservoir. As the oil degrades, however, these antioxidants will gradually disappear. When these antioxidants disappear, this signals that the oil has begun to oxidize, and should be replaced. The inventors have found that by detecting the presence and disappearance of antioxidants such as diphenylamine, and 2,6-dibutylphenol the condition of the oil can be further determined.

Sensors to detect many of the chemical compounds mentioned above are commercially available. Others are not commercially available, and must be custom made for a particular application. One type of sensor which is suitable for the present invention is an array of chemically sensitive field-effect transistors (CHEMFET) employing specially designed selective layers based on conducting polymers. These layers are selectively sensitive for degradation products or antioxidants discussed in the present invention. Sensors of this type are commercially available such as from Nordic Sensor Technologies, Linkoping, Sweden.

Other suitable sensors include chemiresistors employing conducting polymer layers selected for particular degradation products or antioxidants discussed above. A commercial chemiresistor array can be purchased e.g. from Cyrano Sciences, Pasadena or City Technology, Ltd., Portsmouth, England. Another example is an array of mass sensors (thickness shear monitors (TSM) or surface acoustic wave devices) employing non conducting polymer selective layers. Commercial TSM arrays can be obtained e.g. from MOTech, GmbH, Tubingen, Germany.

Another example is an array of optical fiber sensors or optical waveguide sensors employing optically sensitive, selective layers. A sensing array of this type can be obtained from e.g. Illumina, Inc., Massachussets. These are only illustrations of types of chemical sensors that could be used for the present application. The key element of these sensors are the selective layers that have to be developed individually to provide selective response to the individual gases that constitute the "signature" of the used and of the new oil. Such layers are then assembled into an array. The operating principles of the individual sensors are described in J. Janata, "Principles of Chemical Sensors", Plenum, 1988.

Figure 5:
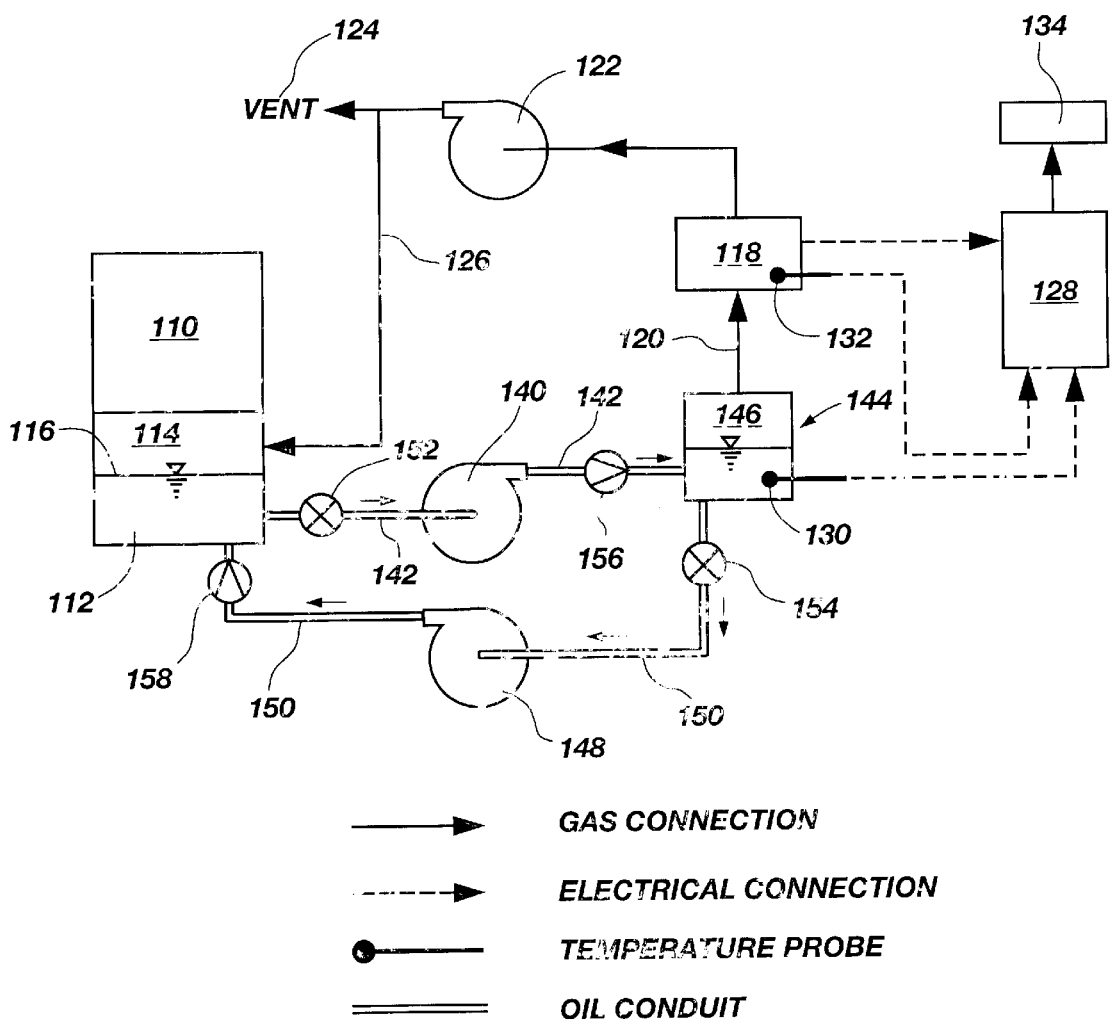
FIG. 5 is a schematic diagram of an alternative embodiment of the invention configured for use with a continuously running oil-utilizing machine.

An alternative embodiment of the present invention could be configured for use with continuously running oil utilizing machines. For example, marine turbine engines, industrial motors, generators, and other oil-utilizing machines experiencing intermittent loads may run for long periods of time between shutdown. In such machines, it becomes impractical or uneconomical to wait for shutdown in order to sense the condition of the oil and create a time and temperature based vapor signature. Accordingly, FIG. 5 depicts an alternative embodiment of the present invention configured for sensing the condition of oil in a continuously running oil utilizing machine 110. As with the other embodiments described above, the machine 110 has an oil reservoir 112 having a head-space 114 above the free surface 116 of the oil.

However, in this embodiment, rather than connecting the sensor array 118 directly to the head-space 114, a hot sample of liquid oil is pumped via pump 140 through conduit 142 to a holding reservoir 144. It will be apparent that rather than using pump 140, the oil sample could alternatively be obtained by tapping a pressurized oil line associated with the machine 110, thus allowing the oil pump of the machine to do the work of sending a sample to the holding reservoir. Other means of placing an oil sample in the holding reservoir could also be utilized. For example, a user could manually open a valve associated with the oil reservoir, and allow oil to flow into a container, then transfer the hot oil from the container to the holding reservoir. Alternatively, the holding reservoir 144 could be located below the elevation of the oil reservoir 112, so that when an appropriate valve is opened the oil will flow into the holding reservoir by means of gravity. Any system which will allow a sample of oil from the oil reservoir 112 to be transported to the holding reservoir 144 will be suitable.

The oil sample pumped into the holding reservoir will give off vapors into the head space 146 of the holding reservoir, and these vapors are allowed to travel via gas conduit 120 to the sensor array 118 for sampling. As with the other embodiments discussed above, the vapors are transported through conduit 120 by means of a micropump 122 which draws the vapors to and through the sensor array. The vapors may then be exhausted to the atmosphere through vent 124 after sensing, or may be circulated back into the machine 110 through conduit 126.

Temperature probes 130 and 132 detect the temperature of the oil sample and sensor array 118, respectively, and this information, along with the sensor array data, are transmitted to a microprocessor 128, which processes the signals in the manner discussed above, to create a time and temperature based vapor signature. In this embodiment, the sampling/analysis sequence is initiated when the oil sample is pumped into the holding reservoir 144, or some preprogrammed delay time thereafter, rather than when an engine or other machine is shut off. Consequently, the machine 110 may continue running without interruption. As described above, the integrated chemical sensing array 118 detects the composition of the vapors in the head space 146 at predetermined temperature intervals as the oil cools down to approximate thermal equilibrium with the outside environment.

It will be apparent that the processor results could be presented in some humanly discernable form through a display 134. Alternatively, the processor results could be directly communicated to other computer devices or machines in order to directly affect the operation of the machine 110. For example, the processor could be interconnected with the electrical control system of the machine, so as to cause the machine to run differently or not at all depending upon the condition of the lubricating oil.

Once the oil in the holding reservoir 144 has completely cooled and the sampling process is complete, the oil may be returned to the oil reservoir 112 by means of second pump 148 and conduit 150, or may be drained from holding reservoir 144 and discarded. Valves 152 and 154 may be provided in the oil conduits 142 and 150 to selectively allow the oil to flow as desired, and checkvalves 156 and 158 may also be provided to prevent backflow. Additionally, rather than having a second pump 148, pump 140 could be configured through selective valving and arrangement of oil conduits to perform both the operations of pumping the hot oil sample to the holding reservoir 144, and returning the cooled sample to the oil reservoir 112.

This self-diagnostic system could be implemented in a wide variety of applications. For example, it would be ideal for the military for engines that are operated under widely varying conditions and loads where time dependent maintenance schedules are difficult to estimate. It could also be used in the civilian sector such as for construction and heavy earth moving machinery, in private automobiles, commercial and private aircraft, ships, and so forth where maintenance schedules are more easily predicted, but may still be unrealistic. Such applications could include internal combustion engines, such as gas or diesel engines, gas turbine or jet engines, and industrial equipment and machines of various kinds. Additionally, hydraulic machines which utilize hydraulically actuated moving parts also use oil which degrades over time. There are a wide variety of such machines, including excavators, loaders, scrapers, dump trucks, power shovels, forklifts, etc. While standard hydraulic fluid typically degrades more slowly than engine lubricating oil, these machines also can benefit from the present invention. Any oil-utilizing machine which operates under intermittent loads such that it is difficult to predict the actual life-expectancy of the oil based on time of use, mileage, etc., is a good application for this system. In all cases, the use of such a system would result in decreased maintenance labor and material costs, decreased environmental waste, and increased useful lifetime of the machines.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A system for determining the condition of oil in an oil-utilizing machine which has an oil reservoir from which oil is pumped to circulate to various parts of the machine, and to which oil is returned when not being circulated, comprising:

a sensor configured for sensing the composition of vapor in said head space in said reservoir by detecting the concentration of gaseous-phase degradation products of oil selected from the group comprising aromatic acids, aromatic aldehydes, polycondensed aromatic hydrocarbons, and antioxidants, and for developing a signal representing said composition; and a processor configured for receiving said signal and for comparing it to predetermined baseline parameters.

2. The system as described in claim 1, further comprising:

a first temperature probe disposed in said oil reservoir for sensing the temperature of the oil, and for developing a signal representing said oil temperature; and a second temperature probe for sensing the temperature of the sensor and for developing a signal representing said sensor temperature; and wherein the processor is configured for receiving the signals from the first and second temperature probes to develop a time and temperature based vapor signature representing the condition of the oil, and for comparing said signature to the predetermined baseline parameters in conjunction with the signal from the sensor to determine whether the sensor signal deviates from said predetermined baseline parameters.

3. The system as described in claim 2 wherein said processor is configured for receiving a series of signals, including first signals and last signals, from said sensor and from said first and second temperature probes at certain times corresponding to predetermined temperatures of the oil as it cools down following shut off of the machine, the first signals being received when the oil-utilizing machine is shut off, and the last signals being received when the oil temperature has reached approximate thermal equilibrium with an external environment, said last signals representing a baseline time and temperature based vapor signature representing the condition of the oil.

4. The system as described in claim 3 wherein said processor is configured for determining whether the series of signals corresponds to the predetermined baseline parameters according to a pattern recognition algorithm.

5. The system as described in claim 1 wherein said sensor comprises a plurality of sensors, each for directly detecting the concentration of one of a plurality of gaseous-phase lubricating oil degradation products in the head space, said gaseous-phase lubricating oil degradation products being selected from the group comprising benzoic acid, benzaldehyde, napthalene, biphenyl, diphenylamine, and 2,6-dibutylphenol.

6. The system as described in claim 1, wherein said oil-utilizing machine is chosen from the group comprising an internal combustion engine, a gas turbine engine, a hydraulic system, and a mechanical transmission.

7. A method for monitoring the condition of lubricating oil in an oil-utilizing machine having an oil reservoir from which oil is pumped to circulate to various parts of the mechanism, and to which oil is returned when not being circulated, comprising the steps of:

(a) operating said machine until the lubricating oil reaches at least a standard operating temperature;

(b) shutting off the machine;

(c) sensing the composition of the vapor within a head space of the oil reservoir with a sensor configured for detecting the concentration of gaseous-phase degradation products of oil selected from the group comprising aromatic acids, aromatic aldehydes, polycondensed aromatic hydrocarbons, and antioxidants within the vapor, and developing a signal representing said composition;

(d) processing the signal representing the composition of the vapor with a processor configured for comparing said signals to predetermined baseline parameters; and (e) repeating steps c through d periodically over a time interval approximately equal to the time required for the oil to cool down to approximate thermal equilibrium with an exterior environment of the oil-utilizing machine, thereby allowing the processor to calculate a time and temperature based vapor signature representing the condition of the oil.

8. The method as described in claim 7, further comprising the steps of (f) sensing the temperature of the oil in the oil reservoir and developing a signal representing said oil temperature;

(g) sensing the temperature of the sensor and developing a signal representing said sensor temperature; and (h) sending the signals representing the temperatures of the oil in the oil reservoir and of the sensor to the processor for processing in conjunction with the signal representing the composition of the vapor, for comparing said signals to the predetermined baseline parameters.

9. The method as described in claim 7, further comprising the step of:

(i) producing a discernable indication to an operator when the processor determines that the time and temperature based vapor signature deviates from said predetermined baseline parameters.

10. The method as described in claim 7, wherein said predetermined baseline parameters are determined by the steps of:
(j) filling said oil reservoir with good oil;
(k) performing steps (a) through (e) to create a time and temperature based vapor signature of the good oil; and
(l) retaining the time and temperature based vapor signature of the good oil in memory in the processor as the predetermined baseline time and temperature based vapor.

11. The method as described in claim 7, wherein said oil-utilizing machine is chosen from the group consisting of an internal combustion engine, a gas turbine engine, a hydraulic system, and a mechanical transmission.

12. The method described in claim 7 wherein the sensor senses the composition of the vapor by more particularly detecting the concentration of gaseous-phase degradation products of oil selected from the group comprising benzoic acid, benzaldehyde, napthalene, biphenyl, diphenylamine, and 2,6-dibutylphenol.

13. A system for determining the condition of oil in an oil-utilizing machine which has an oil reservoir from which oil is pumped to circulate to various parts of the machine, and to which oil is returned when not being circulated, comprising:
means for taking a sample of oil from the oil reservoir while the machine is running;
a holding reservoir for receiving the sample of oil;
a sensor configured for sensing the composition of vapor in the head space of the holding reservoir and for developing a signal representing said composition; and
a processor configured for receiving said signal and for comparing it to predetermined baseline parameters.

14. The system as described in claim 13, further comprising:
a first temperature probe disposed in the holding reservoir for sensing the temperature of the oil sample, and for developing a signal representing said oil sample temperature; and
a second temperature probe for sensing the temperature of the sensor and for developing a signal representing said sensor temperature; and
wherein the processor is configured for receiving the signals from the first and second temperature probes to develop a time and temperature based vapor signature representing the condition of the oil, and for comparing said signature to the predetermined baseline parameters in conjunction with the signal from the sensor to determine whether the sensor signal deviates from said predetermined baseline parameters.

15. The system as described in claim 14 wherein said processor is configured for receiving a series of signals, including first signals and last signals, from said sensor and from said first and second temperature probes at certain times corresponding to predetermined temperatures of the oil as it cools down, the first signals being received immediately after the oil sample is placed in the holding reservoir, and the last signals being received when the temperature of the oil sample has reached approximate thermal equilibrium with an external environment, said last signals representing a baseline time and temperature based vapor signature representing the condition of the oil.

16. The system as described in claim 13 wherein said sensor comprises a plurality of sensors, each for directly detecting the concentration of one of a plurality of gaseous-phase lubricating oil degradation products selected from the group comprising C6–C20 aliphatic carboxylic acids, C6–C14 carboxylic aldehydes, C6–C14 aliphatic esters, C6–C12 unsaturated aldehydes, aromatic acids, aromatic aldehydes, polycondensed aromatic hydrocarbons, and antioxidants.

17. The system as described in claim 13, wherein said oil-utilizing machine is chosen from the-group comprising an internal combustion engine, a turbine engine, a hydraulic system, and a mechanical transmission.

18. A method for monitoring the condition of lubricating oil in an oil-utilizing machine having an oil reservoir from which oil is pumped to circulate to various parts of the mechanism for lubrication thereof and to which oil is returned when not being circulated, comprising the steps of:
(a) removing a sample of oil from the oil reservoir while the machine is running;
(b) placing the sample of oil in a holding reservoir;
(c) pumping a sample of vapor from a head space of the holding reservoir to a sensor;
(d) sensing the composition of the vapor with the sensor and developing a signal representing said composition;
(e) comparing the signal representing the composition of the vapor to predetermined baseline parameters;
(f) repeating steps (c) through (e) periodically over a time interval approximately equal to the time required for the oil sample to reach approximate thermal equilibrium with an exterior environment, thereby allowing the processor to calculate a time and temperature based vapor signature representing the condition of the oil.

19. The method as described in claim 18, further comprising the steps of
(g) sensing the temperature of the oil in the oil reservoir and developing a signal representing said oil temperature;
(h) sensing the temperature of the sensor and developing a signal representing said sensor temperature; and
(i) sending the signals representing the temperatures of the oil in the oil reservoir and of the sensor to the processor for processing in conjunction with the signal representing the composition of the vapor, for comparing said signals to the predetermined baseline parameters.

20. The method as described in claim 18, further comprising the step of:
(j) producing a discernable indication to an operator when the processor determines that the time and temperature based vapor signature deviates from said predetermined baseline parameters.

21. The method as described in claim 18, wherein said predetermined baseline parameters are determined by the steps of:
(k) placing good oil in the oil reservoir of the machine;
(l) running the machine until the good oil reaches at least a standard operating temperature;
(m) performing steps a through f to create a time and temperature based vapor signature of the good oil; and
(n) retaining the time and temperature based vapor signature of the good oil in memory in the processor as the predetermined baseline time and temperature based vapor signature.

22. The method as described in claim 18, wherein said oil-utilizing machine is chosen from the group comprising an internal combustion engine, a gas turbine engine, a hydraulic system, and a mechanical transmission.

23. The method described in claim 18, wherein the sensor senses the composition of the vapor by more particularly detecting the concentration of gaseous-phase degradation products of oil selected from the group comprising C6–C20 aliphatic carboxylic acids, C6–C14 carboxylic aldehydes, C6–C14 aliphatic esters, C6–C12 unsaturated aldehydes, aromatic acids, aromatic aldehydes, polycondensed aromatic hydrocarbons, and antioxidants.

* * * * *